United States Patent [19]

Andrews

[11] Patent Number: 4,725,228
[45] Date of Patent: Feb. 16, 1988

[54] TOOTH CROWN CENTER LOCATING DEVICE

[76] Inventor: Lawrence F. Andrews, 2025 Chatsworth Blvd., San Diego, Calif. 92107

[21] Appl. No.: 45,100
[22] Filed: May 1, 1987

Related U.S. Application Data

[63] Continuation-in-part of Ser. No. 814,067, Dec. 20, 1985, which is a continuation of Ser. No. 734,415, May 14, 1985, abandoned.

[51] Int. Cl.⁴ .............................................. A61C 7/00
[52] U.S. Cl. ......................................... 433/3; 433/72
[58] Field of Search ........................... 433/72, 3, 141; 33/147 D, 143, 149 B, 27, 143 C

[56] References Cited

U.S. PATENT DOCUMENTS 3,906,634  9/1975  Aspel ..................................... 433/3
4,277,237  7/1981  Dermer ................................. 433/72
4,478,576 10/1984  Maijer et al. ......................... 433/3

Primary Examiner—Robert Peshock
Attorney, Agent, or Firm—Townsend and Townsend

[57] ABSTRACT

A tooth crown marking device is comprised of markers at each end. The marker at one end is for marking a specified vertical landmark on the face of a tooth crown. The marker at the other end is for marking the horizontal center of a tooth crown. At that end, there is a pair of locating members adjustably mounted on either side of the horizontal marking arm in such a manner that the marking arm is maintained equidistant from the locating members. Pointers at the end of each locating member are adjusted to span the height of the crown. The horizontal center of a tooth crown is then marked by the marking arm which may be movably mounted on a support column along which the two locating members are mounted or mounted to the support column by a swivel arm.

14 Claims, 6 Drawing Figures

U.S. Patent    Feb. 16, 1988    Sheet 1 of 2    4,725,228
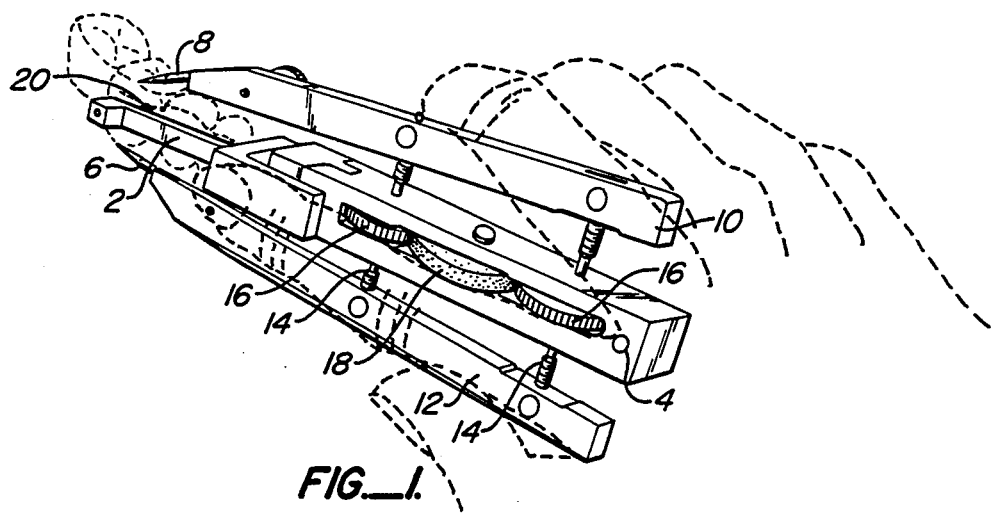
FIG._1.
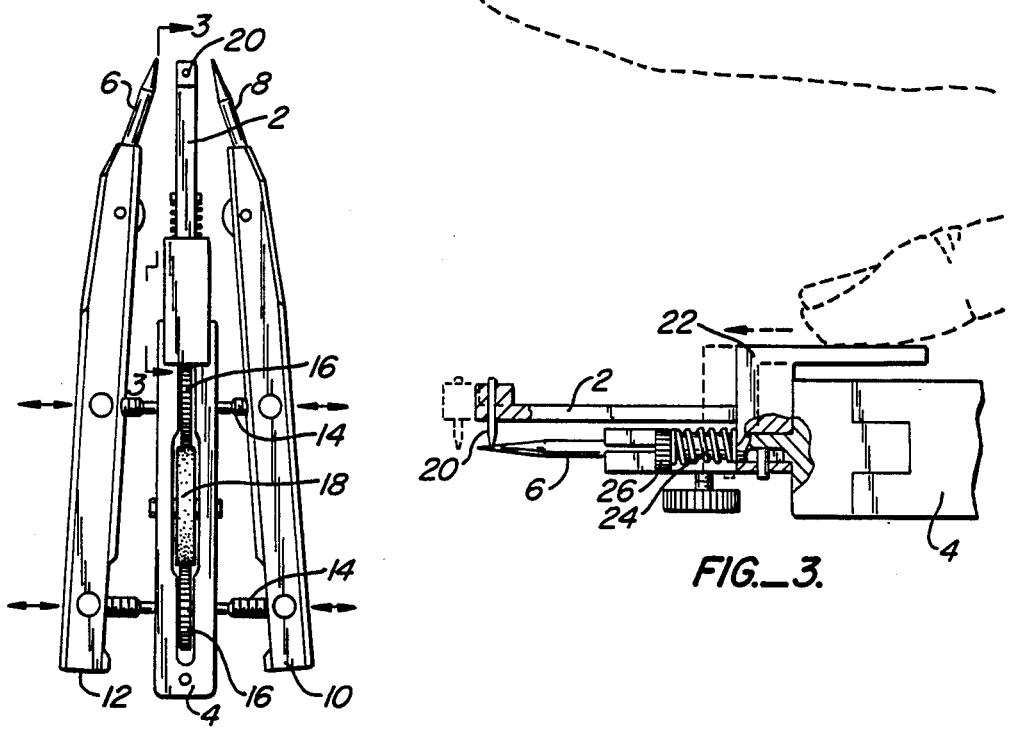
FIG._2.
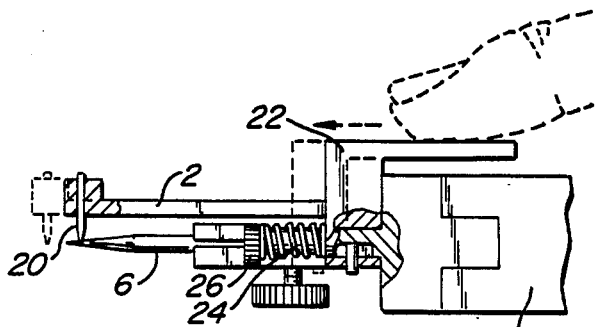
FIG._3.

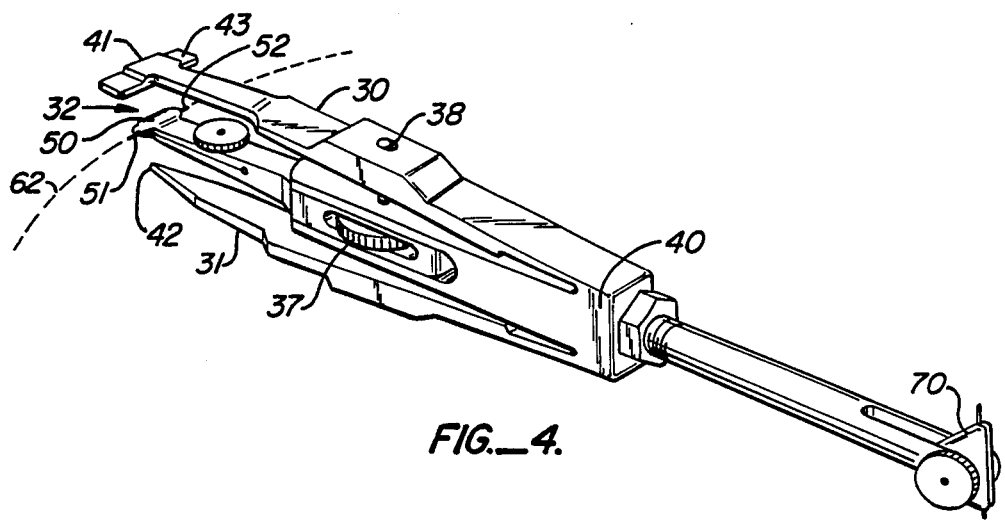
FIG._4.
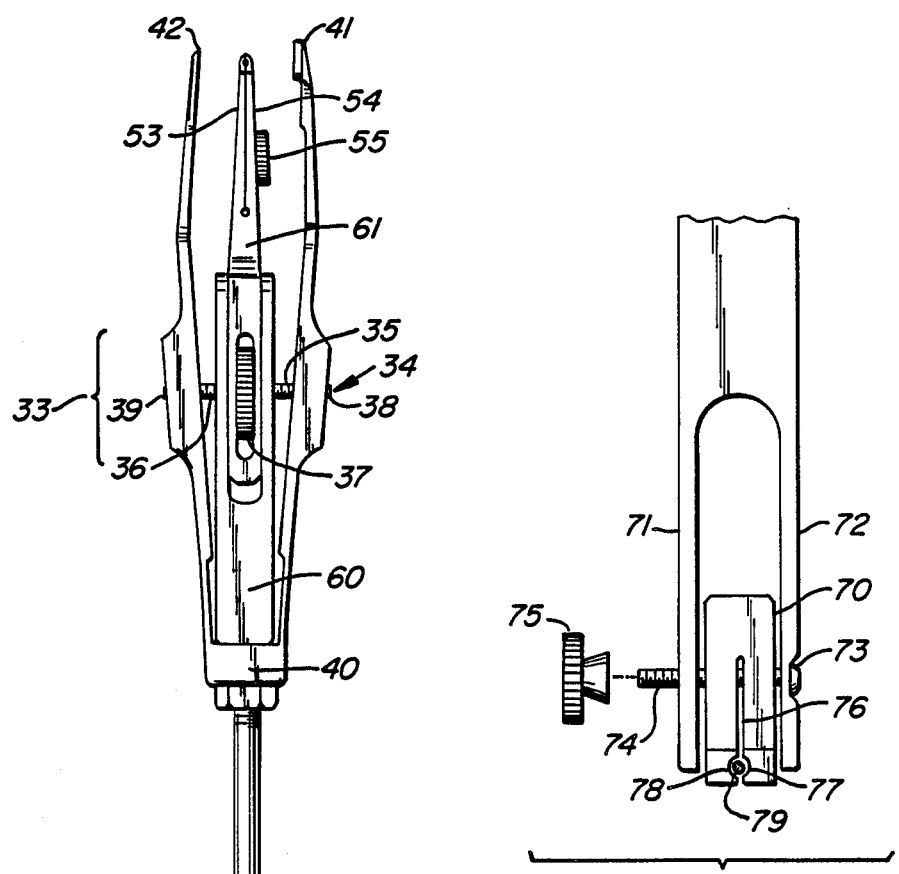
FIG._5.
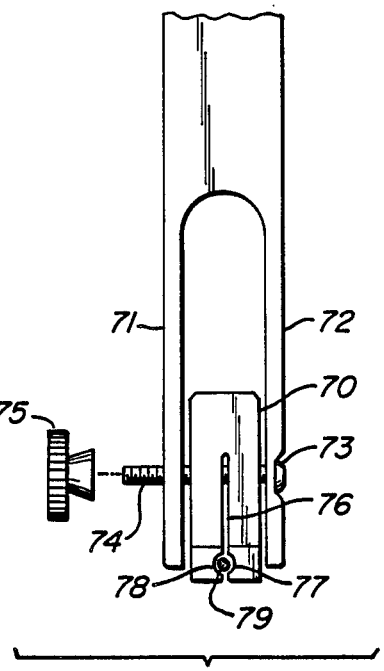
FIG._6.

TOOTH CROWN CENTER LOCATING DEVICE

CROSS REFERENCE TO RELATED APPLICATIONS

This application is a continuation-in-part of application Ser. No. 06/814,067, filed Dec. 20, 1985, which is a continuation of application Ser. No. 06/734,415, filed May 14, 1985 and now abandoned.

BACKGROUND AND SUMMARY OF THE INVENTION

The present invention marks a specified vertical landmark on the face of a tooth crown and measures and marks its horizontal midpoint. These marks serve as the site to which an orthodontic brace is to be precisely located. U.S. Pat. Nos. 3,447,128 and 3,660,900 disclose a system whereby the orthodontist is directed to permanently mount brackets onto the individual teeth at a specified site on each tooth crown. Those patents do not disclose an instrument suitable for locating the proper position for the placement of an orthodontic bracket on a patient's tooth crown.

The broad faces of a tooth crown (not those that are the cutting surfaces) are referred to herein as the crown's "face." While these faces appear flat to the casual observer, they are in fact formed of humps separated by valleys, morphological landmarks resulting from the fusion of embryonic lobes during tooth formation. Molars typically have two such humps on each lateral face while all other teeth have three. Thus, the landmark for the face of a molar is in a valley, while that of other teeth is a hump. They both run vertically. To locate the bracket site, the orthodontist draws two lines, one representing the vertical landmark (the hump or groove) and the other the horizontal center of the vertical landmark. The bracket site is where these two lines cross.

In the past, locating the horizontal center line of the tooth crown required several steps. First, the orthodontist would measure the height of the crown from the gum line to the highest point of the tooth crown. This measurement would then be divided in half. Finally, the orthodontist would again measure the halfway distance from the highest point of the tooth crown to the center, marking the center with a pencil or other suitable marker. This method of finding tooth crown centers would be repeated for every crown scheduled for a bracket. These measurements required skill and dexterity on the part of the orthodontist. For each measurement, the patient's mouth would be oriented so that the orthodontist could manipulate the measuring tools. Repeated measurements required the patient's mouth to be sometimes uncomfortably manipulated to provide access to the tooth for the orthodontist.

The present invention provides a single tool by which the orthodontist can easily locate the horizontal center line of the tooth crown and mark it in a single operation. The invention eliminates the double measurement of each individual crown. The tool virtually eliminates any possibility of error by automatically centering a marker along the tooth. Thus, the level of skill and dexterity required by the orthodontist is greatly reduced. The time for installation and the discomfort to the patient are minimized by use of this invention.

Locating the vertical landmark of a front tooth is done by running a flat marking device down the crown's facial surface so that it will contact and mark only the outermost portion of the middle hump. Highlighting the vertical landmark of a molar is done by finding the center valley with the point of a marking element and running a pointed marker down the length of the valley. In a further embodiment of the present invention, both the horizontal and vertical center lines are marked with the same instrument, the hump with the flat side of the marker, the valley with the point.

The specific features and advantages of the invention can be better understood by reference to the accompanying drawings and the following detailed description.

BRIEF DESCRIPTION OF THE DRAWINGS

FIG. 1 is a perspective illustration of one embodiment of the present invention.

FIG. 2 is a top planar view of the embodiment shown in FIG. 1.

FIG. 3 is view of the embodiment of FIGS. 1 and 2 taken along the line 3—3 in FIG. 2, in partial cutaway.

FIG. 4 is a perspective view of a second embodiment of the present invention.

FIG. 5 is a top view of the embodiment shown in FIG. 4.

FIG. 6 is an end view of the rear of the embodiment shown in FIGS. 4 and 5.

DETAILED DESCRIPTION

FIG. 1 illustrates one embodiment of the tool in use, with the position of the orthodontist's hand and the patient's teeth drawn in phantom lines. The instrument is composed of a marking arm 2 which is movably attached to a support column 4. Spacing is measured by two pointers 6 and 8 which are mounted at the ends of two locating members 10 and 12 respectively, both of which are mounted on either side of the support column 4. The locating members 10 and 12 are adjustably mounted to maintain equal distances between each locating member and the support column by symmetrically threaded spacer rods 14.

Two toothed gears 16 are fixedly mounted to the spacer rods 14 to rotate the spacer rods with respect to the supporting column 4. A smooth gear 18 provides a single control for frictionally operating both toothed gears 16 at once. By rotting the smooth gear 18, the two threaded spacer rods 14 rotate to cause the locating members 10 and 12 to move away from or towards the support column 4. In this way, the distance between the two pointers 6 and 8 is varied.

The marking arm 2 is moved away from the end of the support column 4 along the peg 26 by pushing against the L-shaped piece 22 on which the marking arm 2 is mounted. As may best be seen from FIG. 3, a spring 24 may be provided on peg 26 to bias the marking arm 2 towards the unextended position adjacent to the support column 4. The motion of the marking arm 2 causes the lead 20, which is mounted vertically perpendicular to the marking arm 2, to mark a horizontal line on the tooth center when the pointers 6 and 8 are placed one at the gum line and one at the highest vertical point of the patient's tooth.

Thus, in order to mark the horizontal center line of each tooth, the tool is adjusted by rotating the smooth gear 18 to space the pointers at the top and gum line of the tooth in question. The orthodontist then pushes on the L-shaped piece 22 to cause the marking arm 2 to draw a line at the tooth's center. This marking is repeated at each tooth to be banded.

A second embodiment of the present invention, differing somewhat in form and operation, is shown in FIGS. 4, 5 and 6. Here, as in the embodiment of FIGS. 1, 2 and 3, the instrument contains a pair of locator arms 30, 31, and a marking arm 32 in between. A spacing mechanism 33 (shown most clearly in FIG. 5) operates similarly to the one shown in FIGS. 1 and 2, but consists instead of a single shaft 34 having two halves 35, 36 threaded in opposite directions with a knurled wheel 37 bonded to the shaft at its midpoint. The threaded halves of the shaft pass through holes 38, 39 in the two locator arms respectively, which are threaded to mate with the threaded shaft. Since the two locator arms are joined at their base 40, their forward ends 41, 42 are drawn together and apart by merely turning the knurled wheel 37, which maintains the marking arm 32 in the center at all times.

As in the first embodiment, the forward ends 41, 42 of the locator arms define a gap which the orthodontist adjusts to height of the tooth crown. Unlike the first embodiment, however, the upper locator arm terminates in a flat plate 43. This serves as an occlusal table to be placed on the biting edge of the tooth, thereby facilitating the placement of the instrument and improving the accuracy of the measurement. This also permits the orthodontist to draw the entire instrument back and forth to mark the horizontal center line, keeping the occlusal table in contact with the biting surface. It extends on both sides of center so the instrument can be used for either side of a dental arch. When turned over, it can then be used for either side of the other arch.

It will be noted here, as in the first embodiment, that the marking arm 32 terminates in a marking element 50 protruding in a direction transverse to the axis of the marking arm. A difference here is that the marking element is in two halves 51, 52, protruding in opposite directions on either side of the marking arm. This permits the marking of the teeth on both sides of the arch. The marking element itself is a length of fine pencil lead held in a groove between two fingers 53, 54 at the end of the marker arm. The fingers are forced together by a screw 55 to hold the lead securely in place. The lead protrudes at both ends to provide the two halves of the marking element.

Another distinctive feature of this embodiment is the construction of the marker arm 32 itself. The marker arm consists of a support column 60 and a swivel arm 61. The two are joined by the shaft 34 through loose unthreaded holes, the shaft providing the swivel axis. The marker element 50 is thus permitted to swivel through an arc 62 (FIG. 4) defining a plane which is perpendicular to (and thus bisecting) the width of the gap between the two forward ends of the locator arms. The marker points may thus be moved out of the way during the time the instrument is being adjusted for crown height, then moved into position to mark the tooth.

The rear end of the instrument is used for marking the vertical landmark on the lateral face of a tooth crown (see FIG. 6). The marking element at this end consists of a holder 70 mounted in a pivotal manner between two prongs 71, 72 at the rear end of the instrument, by a pin 73 passing through both prongs and the holder. The pin has a protruding end 74 which is threaded to mate with a nut 75 which is knurled for finger tightening. Tightening of the nut forces the prongs and holder against each other, securing the holder in a fixed position relative to the instrument. In the embodiment shown, the pin 73 is threaded along its entire length. The holes in the prongs and holder through which the pin passes (not shown in the drawings) are a loose fit, not threaded.

The holder itself has an internal slot 76 whose inner surfaces have opposing grooves 77, 78 to retain an elongate marker 79 which may be a pencil lead like the marking element at the forward end of the instrument. The tightening of the nut 75 secures this marker in the holder in the same manner as the screw at the forward end.

For teeth where the vertical landmark is along a convex curvature (i.e., teeth other than molars), the lead 79 should extend at least about one-quarter inch from one end. The side of the lead is then drawn down the lateral face of the tooth crown while the side of the lead is held generally parallel to the lateral face. For convenience in handling the instrument, the holder will preferably be secured at a fixed position such that the lead is at approximately a 45° angle with respect to the axis of the instrument. For molars, where the vertical landmark is a groove or valley between humps, the point at the other end of the lead and holder is used, its angle adjusted to 90° to the face of the molars and the extent of protrusion of the lead from the holder being less extended.

The foregoing is offered primarily for purposes of illustration. It will be readily apparent to those skilled in the art that further variations of the elements of structure and operation described herein may be introduced without departing from the spirit and scope of the invention.

What is claimed is:

1. A device for marking a predetermined location on a tooth crown for the placement of orthodontic braces on a patient's tooth, comprising:
   a tooth marker movably and longitudinally mounted to a support column;
   first and second locating members converging towards said tooth marker and terminating in longitudinally directed points; and
   means for adjustably mounting said first and second locating members spaced apart from and on opposite sides of said support column at first and second user-selected distances from said tooth marker, said adjustable mounting means comprising first and second rotatable shafts mounted transversely through said support column and threadably engaging said spaced apart first and second locating members, each said shaft including a fixed gear mounted thereto in a slot provided along said support column, and a rotable adjustment dial mounted on said support column in said slot between and in frictional engagement with the fixed gears of said first and second rotatable shafts, wherein said shafts are mounted through said locating members at either end of said support column; said first and second locating members terminating in longitudinally directed points.

2. A device for marking a predetermined location on a tooth crown for the placement of orthodontic braces on a patient's tooth comprising:
   a tooth marker longitudinally mounted to a support column for longitudinal movement;
   first and second locating members converging towards said tooth marker and terminating in longitudinally directed points;
   a support column for adjustably mounting said first and second members spaced apart from and on opposite sides of said tooth marker equidistant from said tooth marker; and engaging means whereby the tooth marker is movably coupled to said support column such that said tooth marker moves to mark the tooth at the predetermined distances from said first and second locating members, said engaging means comprising first and second rotable shafts spaced apart from and mounted transversely through said support column and threadably engaging said first and second locating members, wherein each said shaft further comprises a fixed gear mounted thereto in a slot provided along said support column, and a rotatable adjustment dial on said support column in said slot between and in frictional engagement with the fixed gears of said first and second rotatable shafts.

3. A device for marking a specified vertical landmark of a tooth crown and for measuring and marking the midpoint of said tooth crown, comprising:

a support shaft having forward and rear ends;

a first marking element mounted to said forward end and protruding in a direction transverse to said support shaft;

a second marking element mounted to said rear end;

first and second arms mounted to opposing sides of said support shaft and terminating adjacent to said forward end in first and second pointer ends, respectively, defining a gap; and means for varying the width of said gap while maintaining said first marking element equidistant from said first and second pointer ends.

4. A device in accordance with claim 3 in which said second marking element is mounted to said rear end in pivotal manner with respect to a pivot axis transverse to said support shaft.

5. A device in accordance with claim 4 in which said second marking element is a shaft of marking material mounted transverse to said pivot axis.

6. A device in accordance with claim 5 in which said shaft is slidably retained in a holder pivotally mounted to said rear end through said pivot axis.

7. A device in accordance with claim 6 further comprising means for locking said holder in a fixed position with respect to said rear end.

8. A device in accordance with claim 6 further comprising means for locking said shaft in a fixed position with respect to said holder.

9. A device in accordance with claim 3 further comprising a substantially flat plate affixed to one of said first and second pointer ends extending transversely with respect to the width of said gap.

10. A device for marking the horizontal center of a tooth crown, comprising:

a support shaft;

a marking element protruding from said support shaft in a direction transverse thereto;

first and second side arms mounted to opposing sides of said support shaft and terminating in first and second pointer ends respectively, at opposing sides of said marking element, said first and second pointer ends defining a gap; and means for varying the width of said gap while maintaining said marking element equidistant form said first and second pointer ends.

11. A device in accordance with claim 10 in which said marking element is mounted to said support shaft through a swivel arm arranged to swivel in a plane bisecting said gap.

12. A device in accordance with claim 10 in which said marking element is comprised of first and second portions protruding from said support shaft in opposite directions transverse thereto.

13. A device in accordance with claim 11 in which said marking element is comprised of first and second portions protruding from said swivel arm in opposite directions transverse thereto.

14. A device in accordance with claim 10 further comprising a substantially flat plate affixed to one of said first and second pointer ends transversely with respect to the width of said gap.

* * * * *